US00PP33522P3

(12) United States Plant Patent
Flore

(10) Patent No.: US PP33,522 P3
(45) Date of Patent: Sep. 28, 2021

(54) ***PHALAENOPSIS* PLANT NAMED 'MI01248'**

(50) Latin Name: *Phalaenopsis hybrida*
Varietal Denomination: MI01248

(71) Applicant: Febe Flore, Lochristi (BE)

(72) Inventor: Febe Flore, Lochristi (BE)

(73) Assignee: Microflor N.V., Lochristi (BE)

( * ) Notice: Subject to any disclaimer, the term of this patent is extended or adjusted under 35 U.S.C. 154(b) by 0 days.

(21) Appl. No.: 17/073,265

(22) Filed: Oct. 16, 2020

(65) Prior Publication Data

US 2021/0120721 P1 Apr. 22, 2021

Related U.S. Application Data

(60) Provisional application No. 62/973,657, filed on Oct. 17, 2019.

(51) Int. Cl.
*A01H 5/02* (2018.01)
*A01H 6/62* (2018.01)
*A01H 5/00* (2018.01)

(52) U.S. Cl.
USPC ..... Plt./311
CPC ..... *A01H 6/62* (2018.05); *A01H 5/00* (2013.01)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Phalaenopsis* plant named 'MI01248', characterized by its upright plant habit; vigorous growth habit; strong flowering stems; strong and relatively small leaves; freely flowering habit with typically two racemes per plant, each inflorescence with numerous flowers; and large white-colored flowers.

2 Drawing Sheets

Figure 1:
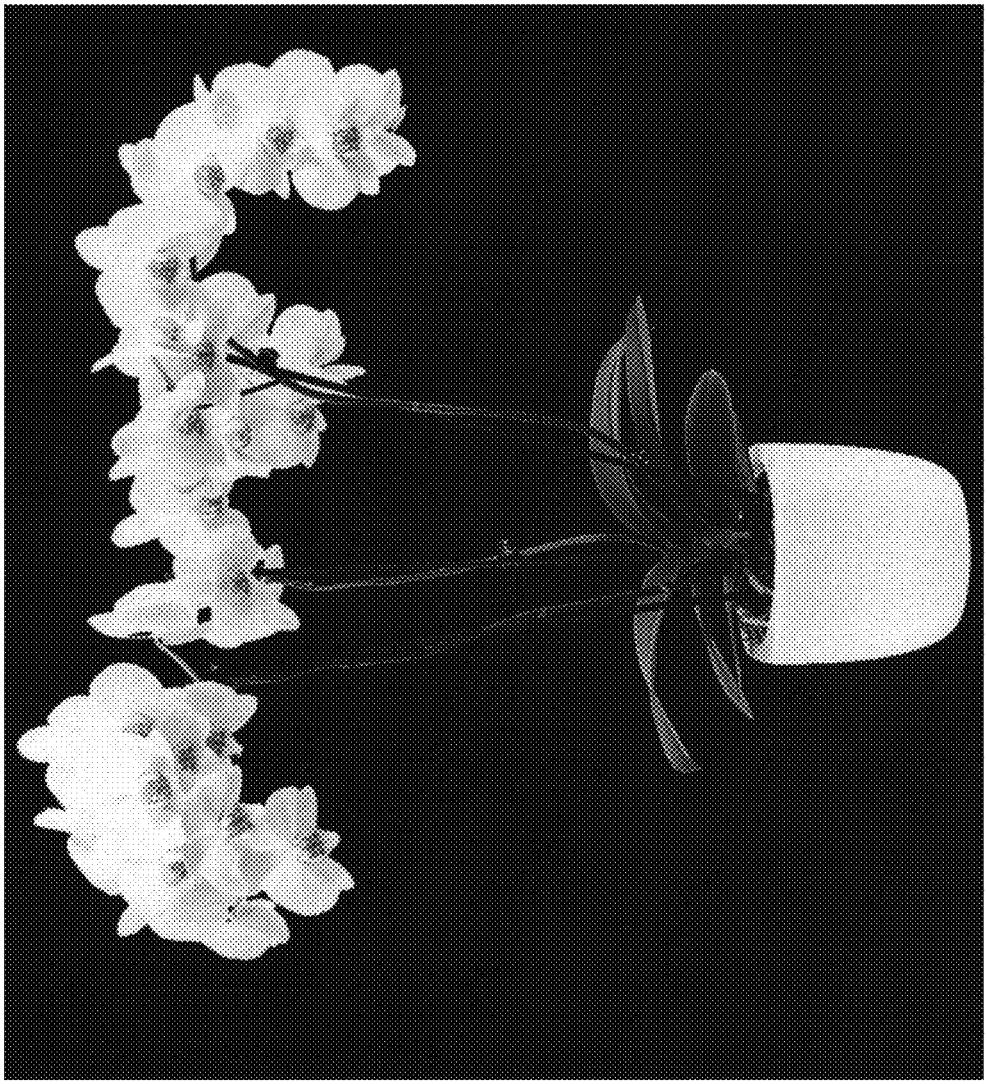
Figure 2:
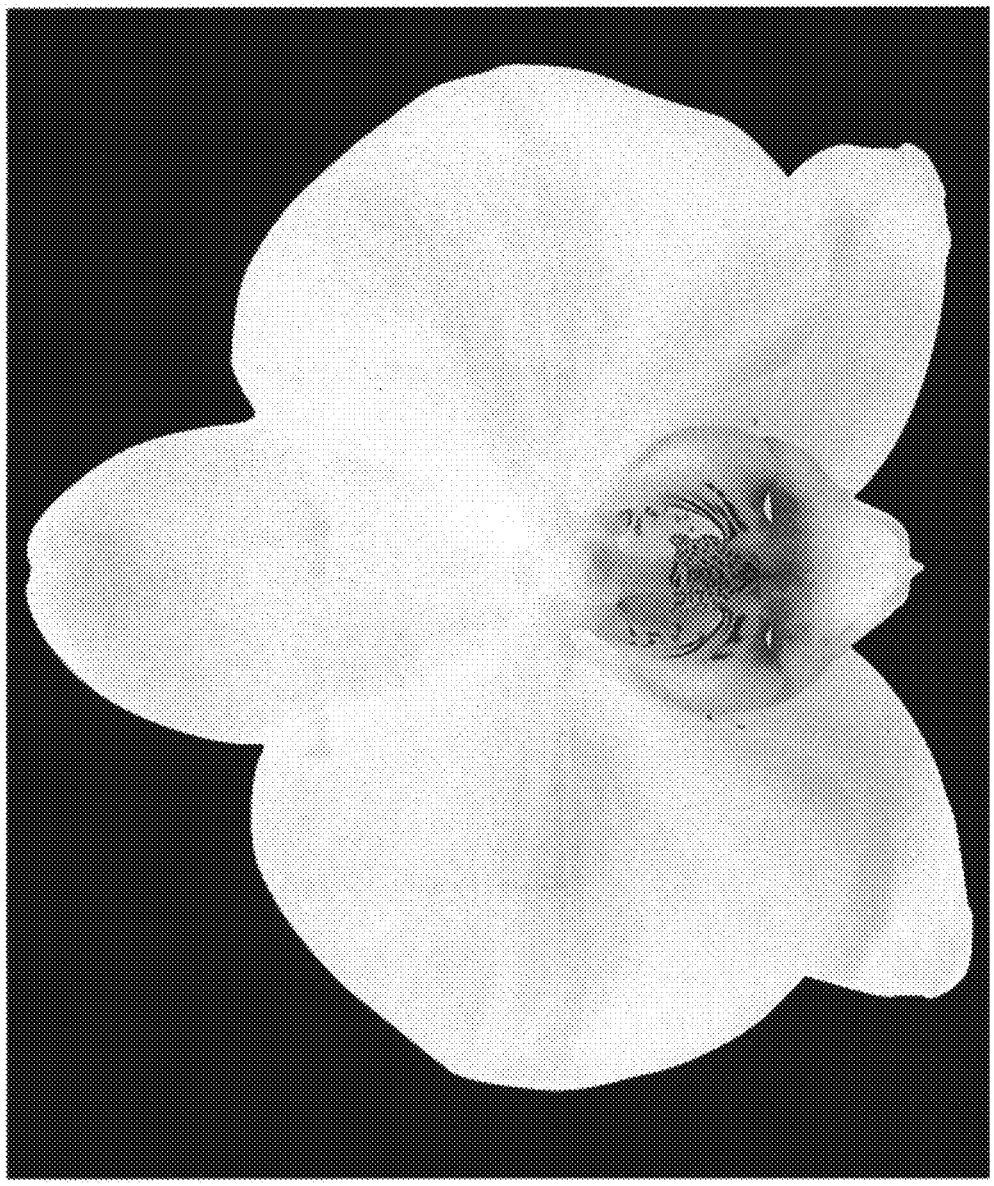

Botanical designation: *Phalaenopsis hybrida.*
Cultivar denomination: 'MI01248'.

CROSS-REFERENCED TO CLOSELY RELATED APPLICATIONS

Title: Varieties of *Phalaenopsis* Plants
Inventor/Applicant: Febe Floré
Provisional application Ser. No. 62/973,657
Filed: Oct. 17, 2019
Inventor/Applicant hereby claim the benefit of this provisional U.S. Patent Application.

STATEMENT REGARDING PRIOR DISCLOSURES BY INVENTOR/APPLICANT

An European Community Plant Breeder's Rights application for the instant plant was filed by the Assignee of the instant application, Microflor N.V. of Lochristi, Belgium on Oct. 24, 2018, application number 2018/2685. Foreign priority is not claimed to this application.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'MI01248'.

The new *Phalaenopsis* plant is a product of a planned breeding program conducted by the Inventor in Lochristi, Belgium. The objective of the breeding program is to develop new freely flowering *Phalaenopsis* plants with good leaf shape and unique and attractive flower coloration.

The new *Phalaenopsis* plant originated from a cross-pollination by the Inventor in 2011 in Lochristi, Belgium of a proprietary selection of *Phalaenopsis hybrida* identified as code number PH00961, not patented, as the female, or seed, parent with a proprietary selection of *Phalaenopsis hybrida* identified as code number PH01170, not patented, as the male, or pollen, parent. The new *Phalaenopsis* plant was discovered and selected by the Inventor as a single flowering plant from within the progeny of the stated cross-pollination grown in a controlled greenhouse environment in Lochristi, Belgium in December, 2014.

Asexual reproduction of the new *Phalaenopsis* plant by in vitro meristem propagation in a controlled environment in Lochristi, Belgium since February, 2016 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'MI01248'. These characteristics in combination distinguish 'MI01248' as a new and distinct *Phalaenopsis* plant:

1. Upright plant habit.
2. Vigorous growth habit.
3. Strong flowering stems.
4. Strong and relatively small leaves.
5. Freely flowering habit with typically two racemes per plant, each inflorescence with numerous flowers.
6. Large white-colored flowers.

Plants of the new *Phalaenopsis* can be compared to plants of the female parent selection. Plants of the new *Phalaenopsis* differ primarily from plants of the female parent selection in the following characteristics:

1. Plants of the new *Phalaenopsis* have larger flowers than plants of the female parent selection.
2. Plants of the new *Phalaenopsis* are more freely flowering than plants of the female parent selection.

Plants of the new *Phalaenopsis* can be compared to plants of the male parent selection. Plants of the new *Phalaenopsis* differ primarily from plants of the male parent selection in the following characteristics:

1. Plants of the new *Phalaenopsis* are shorter than plants of the male parent selection.
2. Plants of the new *Phalaenopsis* have shorter leaves than plants of the male parent selection.
3. Plants of the new *Phalaenopsis* have smaller flowers plants of the male parent selection.

Plants of the new *Phalaenopsis* can be compared to plants of *Phalaenopsis hybrida* 'MI00901', disclosed in U.S. Plant Pat. No. 30,686. In side-by-side comparisons, plants of the new *Phalaenopsis* differ primarily from plants of 'MI00901' in the following characteristics:

1. Plants of the new *Phalaenopsis* have shorter inflorescences than plants of 'MI00901'.
2. Plants of the new *Phalaenopsis* have smaller flowers than plants of 'MI00901'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet is a side perspective view of a typical flowering plant of 'MI01248' grown in a container.

The photograph on the second sheet is a close-up view of a typical flower of 'MI01248'.

DETAILED BOTANICAL DESCRIPTION

The aforementioned photographs and following observations and measurements describe plants grown during the summer in 12-cm containers in a glass-covered greenhouse in Lochristi, Belgium and under cultural practices typically used in commercial *Phalaenopsis* production. During the production of the plants, day and night temperatures ranged from 18° C. to 29° C. and light levels ranged from 150 Watt/m$^2$ to 375 Watt/m$^2$. Plants were 62 weeks old when the photographs and description were taken. In the following description, color references are made to The Royal Horticultural Society Colour Chart, 2015 Edition, except where general terms of ordinary dictionary significance are used.

Botanical classification: *Phalaenopsis hybrida* 'MI01248'.

Parentage:

*Female parent*.—Proprietary selection of *Phalaenopsis hybrida* identified as code number PH00961, not patented.

*Male parent*.—Proprietary selection of *Phalaenopsis hybrida* identified as code number PH01170, not patented.

Propagation:

*Type*.—By in vitro meristem propagation.

*Time to initiate roots, summer*.—About nine to ten weeks at temperatures about 26° C.

*Time to initiate roots, winter*.—About ten to eleven weeks at temperatures about 26° C.

*Time to produce a rooted young plant, summer*.—About 140 to 160 days at temperatures about 26° C.

*Time to produce a rooted young plant, winter*.—About 150 to 180 days at temperatures about 26° C.

*Root description*.—Thick, fleshy; typically grey green in color, towards the apex, close to light green; actual color of the roots is dependent on substrate composition, water quality, fertilizer, substrate temperature and age of roots.

*Rooting habit*.—Low to non-branching; sparse.

Plant description:

*Plant form and growth habit*.—Herbaceous epiphyte; upright plant habit with typically two branched racemes per plant, each inflorescence with numerous flowers; monopodial; vigorous growth habit and rapid growth rate.

*Plant height, substrate level to top of foliar plane*.—About 12 cm.

*Plant height, substrate level to top of inflorescences*.—About 48 cm.

*Plant diameter or spread*.—About 35.5 cm.

Leaf description:

*Arrangement and quantity*.—Distichous, simple; sessile; about six leaves per plant.

*Length*.—About 19 cm.

*Width*.—About 9.5 cm.

*Aspect*.—Mostly flat to slightly arching.

*Shape*.—Lanceolate to elliptic.

*Apex*.—Obtuse to unequal acute.

*Base*.—Sheathing.

*Margin*.—Entire; slightly revolute towards the apex.

*Texture and luster, upper and lower surfaces*.—Slightly furrowed, glabrous; moderately glossy.

*Venation pattern*.—Camptodromous.

*Color*.—Developing leaves, upper surface: Close to NN137A. Developing leaves, lower surface: Close to 144A. Fully expanded leaves, upper surface: Close to between 137A and 146A; venation, close to 144B. Fully expanded leaves, lower surface: Close to 144A; venation, close to 144B.

Inflorescence description:

*Appearance and flowering habit*.—Showy zygomorphic flowers arranged on axillary branched racemes; typically two racemes per plant; each inflorescence with about ten open flowers; flowers face outwardly on arching inflorescences supported by upright peduncles; flowers with three petals, two lateral petals and one center petal transformed into a labellum and three sepals.

*Fragrance*.—None detected.

*Time to flower*.—Plants begin flowering about 17 weeks after an inductive cooling period.

*Flower longevity*.—Long flowering period, individual flowers maintain good substance for about 19 weeks on the plant; flowers not persistent.

*Inflorescence length* (*lowermost flower to inflorescence apex*).—About 19.7 cm.

*Inflorescence width*.—About 14.6 cm by 23 cm.

*Flower buds*.—Height: About 7 mm. Diameter: About 6 mm. Shape: Ovate. Color: Close to 145C.

*Flower diameter*.—About 9.2 cm.

*Flower depth*.—About 2.8 cm.

*Petals, quantity and arrangement*.—Three, two lateral petals and one center petal transformed into a labellum.

*Lateral petals*.—Length: About 4.4 cm. Width: About 5.3 cm. Shape: Reniform. Apex: Rounded. Margin: Entire. Texture and luster, upper and lower surfaces: Smooth, glabrous, velvety; matte. Color: When opening, upper and lower surfaces: Close to NN155D. Fully opened, upper and lower surfaces: Close to NN155D.

*Labellum*.—Appearance: Tri-lobed with two lateral lobes and a central lobe. Length: About 3.2 cm. Width: About 2.4 cm. Shape, lateral lobes: Ovate. Shape, central lobe: Roughly rhomboidal to deltoid. Apex, lateral lobes: Obtuse. Apex, central lobe: Cleft with two moderately long narrow recurved cirrose tips. Margins, lateral and central lobes: Entire. Texture and luster, upper and lower surfaces: Smooth, glabrous, moderately velvety; matte. Callosities: Located at the base of the labellum and attachment point of the lateral petals; about 6 mm in length, about 5.5 mm in width and about 6 mm in height. Color: When opening and fully opened, upper surface: Lateral lobes: Close to NN155D; towards the apex, tinged with close to 9A; towards the base tinged with close to 180A and with spots, close to 61A. Central lobe: Close to 155D; towards the apex, tinged with close to 9A; towards the base, tinged with close to 180A. Callosities: Close to 12A; spots, close to 61A. When opening and fully opened, lower surface: Lateral lobes: Close to NN155D; towards the apex, tinged with close to 9A. Central lobe: Close to 155D; towards the apex, tinged with close to 9A; towards the base, tinged with close to 180A. Callosities: Close to 12A; spots, close to 61A.

*Sepals*.—Quantity and arrangement: Three, two lower lateral sepals and one upper dorsal sepal. Length, lateral sepal: About 4.7 cm. Width, lateral sepals: About 2.7 cm. Length, dorsal sepal: About 4.4 cm. Width, dorsal sepal: About 2.9 cm. Shape, lateral sepals: Ovate. Shape, dorsal sepal: Ovate to broadly ovate. Apex, lateral sepals: Obtuse to broadly and bluntly acute. Apex, dorsal sepal: Obtuse. Base, lateral and dorsal sepals: Acute to obtuse. Margin, lateral and dorsal sepals: Entire. Texture and luster, lateral and dorsal sepals, upper and lower surfaces: Smooth, glabrous, velvety; matte. Color, lateral sepals: When opening, upper surface: Close to between 155D and 145C; spots, close to 77A. When opening, lower surface: Close to between 155D and 145C. Fully opened, upper surface: Close to 155D; spots, close to 77A. When opening, lower surface: Close to between 155D and 145C. Color, dorsal sepal: When opening, upper and lower surfaces: Close to 155D. Fully opened, upper and lower surfaces: Close to 155D.

*Peduncles*.—Length: About 54 cm. Diameter: About 5 mm. Strength: Very strong. Aspect: Upright to about 15° from vertical. Texture and luster: Smooth, glabrous; matte. Color: Close to 200C densely covered with fine dots, close to 146A.

*Pedicels*.—Length: About 4.5 cm. Diameter: About 3 mm. Strength: Moderately strong. Aspect: About 85° from peduncle axis. Texture and luster: Smooth, glabrous; matte. Color: Close to 155D; proximally, close to 154A with dots, close to 200C.

*Reproductive organs*.—Androecium: Column length: About 9 mm. Column width: About 5 mm. Column color: Close to 155A. Pollinia quantity: Two. Pollinia diameter (per two pollinia): About 2 mm. Pollinia color: Close to 21A. Gynoecium: Stigma length: About 3 mm. Stigma width: About 4 mm. Stigma shape: Reniform. Stigma color: Close to N155A. Ovary length: About 8 mm. Ovary diameter: About 3 mm. Ovary color: Close to N75C to N75D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures of about 40° C. and suitable for USDA Hardiness Zone 10.

It is claimed:

1. A new and distinct *Phalaenopsis* plant named 'MI01248' as illustrated and described.

* * * * *